US00PP12867P2

(12) United States Plant Patent
Henny

(10) Patent No.: US PP12,867 P2
(45) Date of Patent: Aug. 20, 2002

(54) AGLAONEMA PLANT NAMED 'EMERALD BAY'

(75) Inventor: Richard Jay Henny, Tavares, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 09/774,367

(22) Filed: Feb. 1, 2001

(51) Int. Cl.[7] ..... A01H 5/00

(52) U.S. Cl. ..... Plt./376

(58) Field of Search ..... Plt./376

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Aglaonema plant named 'Emerald Bay', characterized by its freely basal branching growth habit; attractive and unique variegated foliage; leaves are silvery gray in the center, with random dark green and gray-green blotches towards the margins, and dark green margins; and light green-colored petioles.

2 Drawing Sheets

BACKGROUND OF THE INVENTION

The present Invention relates to a new and distinct cultivar of Aglaonema plant, botanically known as *Aglaonema hybrida*, and hereinafter referred to by the name 'Emerald Bay'.

The new Aglaonema is a naturally-occurring whole plant mutation of the *Aglaonema hybrida* cultivar 39303, disclosed in U.S. Plant Pat. No. 10,140. The new Aglaonema was discovered by the Inventor in a controlled environment in Apopka, Fla., as a single plant within a large population of tissue-cultured plants of the cultivar 39303. The selection of this plant was based on its attractive and unique variegated foliage. Plants of the new Aglaonema differ primarily from plants of the parent cultivar in coloration as plants of the new Aglaonema lack yellow coloration in the stems, leaf petioles and leaves.

Asexual propagation of the new cultivar by stem cuttings in Apopka, Fla., since the summer of 1998, has shown that the unique features of this new Aglaonema plant are stable and reproduced true to type in successive generations of asexual propagation.

SUMMARY OF THE INVENTION

The new Aglaonema has not been observed under all possible environmental conditions. The phenotype may vary somewhat with variations in environment such as temperature, light intensity, water status, fertilizer level and propagation procedures, without, however, any variance in genotype.

The following traits have been repeatedly observed and are determined to be the unique characteristics of 'Emerald Bay'. These characteristics in combination distinguish 'Emerald Bay' as a new and distinct cultivar:

1. Freely basal branching growth habit.

2. Attractive and unique variegated foliage; leaves are silvery gray in the center, with random dark green and gray-green blotches towards the margins, and dark green margins.

3. Light green-colored petioles.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Aglaonema.

The photograph at the top of the first sheet comprises a side perspective view of a typical plant of 'Emerald Bay'.

The photograph at the bottom of the first sheet comprises a close-up view of a typical stem and leaves of 'Emerald Bay'.

The photograph on the second sheet comprises a close-view of typical leaves showing the upper (top) and lower (bottom) surfaces of 'Emerald Bay'.

DETAILED BOTANICAL DESCRIPTION

The following observations, measurements and comparisons describe 24-week old plants (from rooted 4 to 5-leaf stem cuttings) grown in Apopka, Fla., under commercial greenhouse conditions in 15-cm containers.

In the following description, color references are made to The Royal Horticultural Society Colour Chart, 1995 Edition, except where general terms of ordinary dictionary significance are used.

Botanical classification: *Aglaonema hybrida* cultivar Emerald Bay.

Parentage: Naturally-occurring whole plant mutation of *Aglaonema hybrida* cultivar 39303, disclosed in U.S. Plant Pat. No. 10,140.

Propagation:

*Type.*—By stem cuttings.

*Time to initiate roots.*—Summer: About 28 days at 32° C. Winter: About 35 days at 20° C.

*Time to develop roots.*—Summer: About 140 days at 32° C. Winter: About 170 days at 20° C.

*Root description.*—Thick and freely branching with fine lateral roots.

Plant description:

*Plant shape.*—Upright, broad inverted triangle, symmetrical.

*Growth habit.*—Erect when young, becoming outwardly arching as leaves develop. Freely basal branching with three to five basal branches forming per plant. Appropriate for 15-cm containers.

*Plant height.*—About 35 to 40 cm from soil level to top of leaf plane.

*Plant spread.*—About 50 to 60 cm.

*Stem color.*—Darker green, 147B to 147C, areas blending into lighter olive green, 152A and 152C to 152D, areas. Stems are usually not visible due to the clasping petiole wings that surround the stems.

*Foliage description.*—Length: About 30 to 33 cm. Width: About 10 to 11 cm. Shape: Lanceolate. The widths of the lamina on either side of the midrib tend to be slightly unequal resulting in a slight curving of the leaf blade towards the narrower side. Apex: Acuminate. Base: Obtuse, occasionally slightly oblique. Margin: Entire. Texture: Leathery, smooth, glabrous. Aspect: Veins are sunken on upper surface giving a rugose appearance and protrude prominently on the lower surface. Color: Upper surface: Sivery gray, closest to 191A to 191B, covers the entire center of the leaf and extends about halfway from the leaf midrib to the margin where random dark green, 147A, and smaller gray-green, 189A, blotches are present along an irregular line; margin, dark green, 147A. Lower surface: Uniformly light green, 137C, with several green, 147B, small spots along the entire length of the midrib, the majority of the spots are within 1 cm of either side of the midrib. Midrib: Silver gray, closest to 191A to 191B, similar to the leaf center. Primary veins: Similar in color as the surrounding tissue. Petiole: Center, 145C; outer wings, 147A with many random small blotches, 147B.

Inflorescence description: Mature plants have been observed to flower in the spring under greenhouse conditions in Apopka, Fla. However, subsequent clonal selection has produced plants with few to no inflorescence. Seed development has not been observed.

Disease resistance: Plants of the new Aglaonema have not been shown to be resistant to pathogens common to Aglaonema.

It is claimed:

1. A new and distinct cultivar of Aglaonema plant named 'Emerald Bay', as illustrated and described.

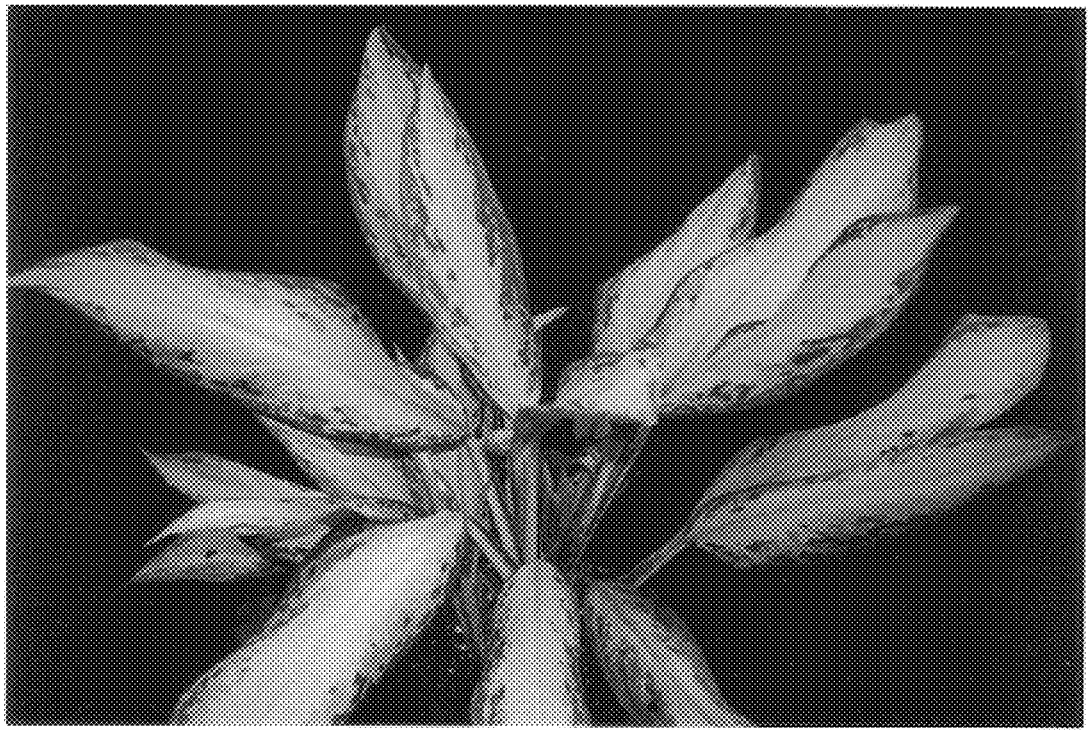
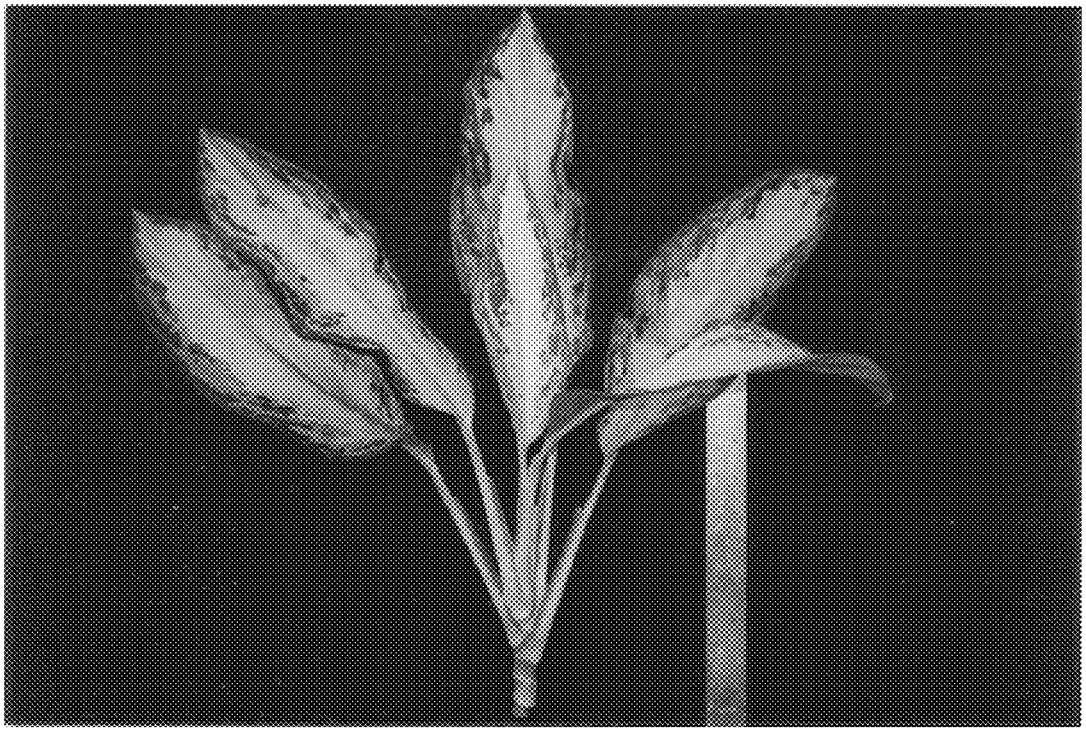

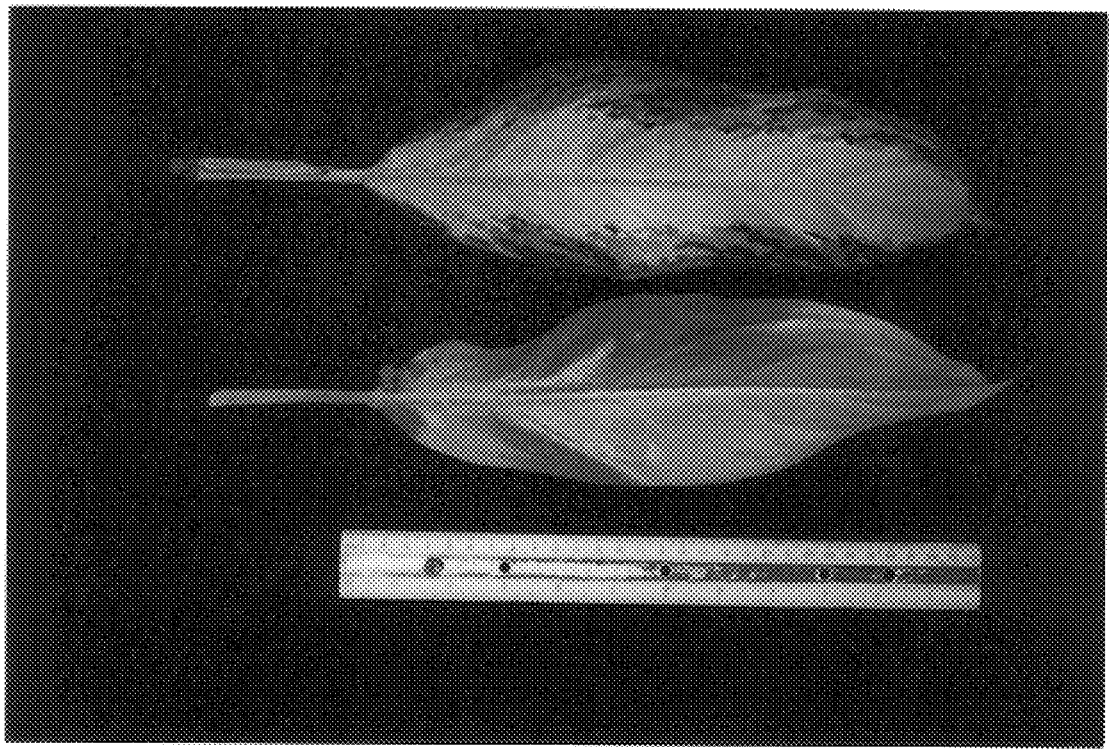

* * * * *